United States Patent [19]
Doble et al.

[11] Patent Number: 5,830,907
[45] Date of Patent: Nov. 3, 1998

[54] APPLICATION OF RILUZOLE IN THE TREATMENT OF NEUROLOGICAL LESIONS ASSOCIATED WITH TRAUMA

[75] Inventors: Adam Doble; Erik Louvel, both of Paris; Jeremy Pratt, Charenton le Pont; Jean-Marie Stutzmann, Villecresnes, all of France

[73] Assignee: Rhone-Poulenc Rorer, S.A., Antony, France

[21] Appl. No.: 424,529

[22] PCT Filed: Dec. 10, 1993

[86] PCT No.: PCT/FR93/01229

§ 371 Date: May 30, 1995

§ 102(e) Date: May 30, 1995

[87] PCT Pub. No.: WO94/13288

PCT Pub. Date: Jun. 23, 1994

[30] Foreign Application Priority Data

Dec. 16, 1992 [FR] France .................................. 92 15148

[51] Int. Cl.⁶ .................................................. A61K 31/425
[52] U.S. Cl. .............................................................. 514/367
[58] Field of Search ............................................. 514/367

[56] References Cited

U.S. PATENT DOCUMENTS

| | | | |
|---|---|---|---|
| 4,370,338 | 1/1983 | Mizoule . | |
| 4,826,860 | 5/1989 | Johnson et al. . | |
| 4,918,090 | 4/1990 | Johnson et al. . | |
| 5,240,948 | 8/1993 | Gueremy et al. | 514/637 |
| 5,403,861 | 4/1995 | Goldin et al. | 514/634 |
| 5,527,814 | 6/1996 | Louvel | 514/367 |

FOREIGN PATENT DOCUMENTS

| | | |
|---|---|---|
| 0 050 551 | 4/1982 | European Pat. Off. . |
| 0 282 971 | 9/1988 | European Pat. Off. . |

OTHER PUBLICATIONS

Neuroscience Letters, vol. 140, No. 2, 22 Jun. 1992, pp. 225–230, J. Pratt et al., "Neuroprotective Actions of Riluzole in Rodent . . . ".

The Journal Of Neuroscience, vol. 9, No. 11, 1989, pp. 3720–3727, C. Malgouris et al., "Riluzole, A Novel Antiglutamate, Prevents . . . ".

Soc. Neurosc. Abstr., vol. 14, 1988, pp. 774, V.O. Gardner et al. "Excitotoxic Mediated Spinal Cord Damage: Possible Role . . . ".

Acta Neurochirurgica, vol. 55, No. SUP, 1992, pp. 49–55, R. Bullock et al., "Prevention of Post–Traumatic Excitotoxic Brain Damage . . . ".

European Journal of Pharmacology, vol. 175, No. 2, 1990, pp. 165–174, A.I. Faden et al., "Effects of Competitive and Non–Competotive . . . ".

Science, vol. 244, No. 4906, 1989, pp. 798–800, A.I. Faden et al., The Role of Excitatory Amino Acids and NMDA Receptors in Traumatic . . .

Neuropharmacology, vol. 24, No. 11, 1985, pp. 1085–1092, J. Benavides et al., "2–Amino–6–Trifluoromethoxy Benzothiazole, A Possible . . . ".

Neuroscience Letters, vol. 147, No. 2, 1992, pp. 209–212, A. Cheramy et al., "Riluzole Inhibits the Release of Glutamate in the Caudate . . . ".

Malgouris et al, "Riluzole, a Novel Antiglutamate, Prevents Memory Loss and Hippocampal Neuronal Damage in Ischemic Gerbile", Journal of Neuroscience, vol. 9, No. 11, Nov., 1989, pp. 3720–3727.

D.W. Choi, "Glutamate Neurotoxicity and Disease of the Nervous System," Neuron, vol. 1, pp. 623–634, (Oct. 1988).

D.W. Choi, "Methods for Antagonizing Glutamate Neurotoxicity," Cerebrovascular and Brain Metabolism Reviews, vol. 2, pp. 105–147, (1990).

A.I. Faden et al., "Pharmacological Strategies in CNS Trauma," TiPS, vol. 13, pp. 29–35, (Jan. 1992).

*Primary Examiner*—Keith D. MacMillan
*Attorney, Agent, or Firm*—Finnegan, Henderson, Farabow, Garrett & Dunner, L.L.P.

[57] ABSTRACT

Application of riluzole or its pharmaceutically acceptable salts in the treatment of neurological lesions related to traumatic injuries, especially spinal, cranial or cranial-spinal injuries.

6 Claims, No Drawings

APPLICATION OF RILUZOLE IN THE TREATMENT OF NEUROLOGICAL LESIONS ASSOCIATED WITH TRAUMA

This application is a 371 of PCT/FR93/01229, filed Dec. 10, 1993, which claims priority to FR92-15148 filed Dec. 16, 1992.

FIELD OF THE INVENTION

The present invention relates to a novel therapeutic application of riluzole or the pharmaceutically acceptable salts of this compound.

BACKGROUND OF THE INVENTION

Riluzole is known to be useful as an anticonvulsant, anxiolytic and hypnotic medicinal product (Patent EP 50,551), in the treatment of schizophrenia (EP 305,276), in the treatment of sleep disorders and depression (EP 305,277), in the treatment of cerebrovascular disorders and as an anesthetic (EP 282,971).

DESCRIPTION OF THE INVENTION

It has now been found, surprisingly, that this compound may also be used in the treatment of neurological lesions associated with trauma, and especially with spinal, cranial or craniospinal trauma.

The activity of this product has been demonstrated on lesions of the spinal cord in the model of cord lesion in rats by the technique of compression by means of a balloon at lumbar medullary level described by Zileli et al., Acta Neurochi, 108, 140–147 (1991) and Pointillart et al., J. of Neurotrauma, 10, 2, 201–213 (1993). Riluzole (4 mg/kg i.v./day) is injected 5 minutes after the trauma, and then every day for 7 days. In the untreated group (10 rats), 2 rats died on the third day, 7 rats did not recover from their lesion and 1 rat recovered from its lesion on the seventh day. In the group treated with riluzole (10 rats), 1 rat died on the fifth day, 1 rat did not recover from its lesion and 8 rats regained their motility and their somatosensory evoked potential (SEP) between the third and the seventh day.

The activity of this product with respect to lesions of the spinal cord has also been demonstrated either using the model of cord lesion in rats by the technique of ventral compression described by E.C. Benzel et al, Journal of Spinal Disorders, 3, 4, 334–338 (1990), or using the model of traumatic tetraplegia induced by compression of the spinal cord with an inflatable microballoon according to the technique described by D. Martin et al., Journal of Neuroscience Research, 32, 539–550 (1992).

In these tests, riluzole decreases the animals' neurological deficit (paraplegia) associated with lesion of the spinal cord as well as histopathological lesions (necrosis of the cord). This decrease is generally equal to or greater than 5%.

The activity of this product is also demonstrated in the model of medullary lesions on 15 "Fauve de Bourgogne" rabbits weighing 4 kg (±200 g). The rabbits are divided into three groups and receive traumas of variable size, according to the following protocol:

a) preparation of animals: rabbits are injected intramuscularly with 5 mg of valium® and 1/16 mg of atropine. 30 minutes later, an isotonic saline perfusion is instituted and the rabbits are anesthetized by slow intravenous injection of 40 mg/kg of Nesdonal®. A cardioscope is installed, since the animal may display a lasting apnoea with bradycardia, particularly on reinjection of Nesdonal®.

b) recording of somatosensory evoked potentials (SEP): these recordings specify the integrity of the sensory pathways of the cord. Stimulation is carried out on the internal popliteal sciatic (IPS) nerve. The intensity of stimulation is calculated so as to evoke a potential in the large-calibre sensory fibers, this being produced at the threshold level of motor stimulation (minimal movement of the foot). The signal is picked up by means of an electrode planted in the scalp in the contralateral parietal cortex. A reference electrode is placed on the median line of the scalp at frontal (Fz) level. An SEP is recorded before inserting the probe to serve as reference.

c) production of trauma: trauma is produced by inflating the balloon of a Fogarty French 3 probe placed in the spinal canal in an extradural position. To this end, a lower lumbar laminectomy is carried out. Opening of the yellow ligament enables the probe to be inserted up to the level of the first lumbar vertebra, and the operating wound is closed up. A further SEP is recorded to check for the absence of functional lesion during insertion of the probe. The lesion is then produced by inflating the balloon with variable amounts of air (0.2, 0.4 and 0.55 ml of air), and the probe is thereafter withdrawn. A further SEP measurement is carried out immediately after the trauma and is compared (amplitudes and latencies) with the reference SEP.

d) The products are injected intraperitoneally once daily for 5 days, at doses of between 1 and 8 mg/kg.

e) histology: a spine/cord block that includes the damaged level is removed and placed in 10% formalin. One week later, the cord is extracted from the block (this fixing time appears to be necessary in order to avoid a post-mortem lesion). A haemorrhagic area visible to the naked eye shows the level of the trauma. Serial histological sections specify the extent of the lesions.

f) results: riluzole enables the neurological deficit associated with lesion of the spinal cord to be decreased, the sensory neurological pathways to be protected and the haemorrhagic necrotic area within the grey matter of the spinal cord to be decreased. These decreases are generally equal to or greater than 5%.

The activity of this product in cranial trauma has also been demonstrated in rats according to the technique described by T. K. McIntosh et al., Central Nervous System Trauma, 4, 2, 119–134 (1987).

In this test, riluzole improves the neurological score of animals which have undergone a cranial trauma and reduces the necrotic lesions. This decrease is generally equal to or greater than 5%.

As pharmaceutically acceptable salts, the addition salts with inorganic acids, such as hydrochloride, sulphate, nitrate or phosphate, or organic acids, such as acetate, propionate, succinate, oxalate, benzoate, fumarate, maleate, methanesulphonate, isethionate, theophyllineacetate, salicylate, phenolphthalinate or methylenebis(β-hydroxynaphthoate), or substitution derivatives of these derivatives, may be mentioned in particular.

The medicinal products consist at least of riluzole, in free form or in the form of an addition salt with a pharmaceutically acceptable acid, in the pure state or in the form of a composition in which it is combined with any other pharmaceutically compatible product, which may be inert or physiologically active. The medicinal products according to the invention may be employed orally or parenterally.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica, under a stream of argon. These compositions can also comprise substances other than diluents, for example one or more lubricants such as magnesium stearate or talc, a coloring, a coating (dragées) or a varnish.

As liquid compositions for oral administration, pharmaceutically acceptable solutions, suspensions, emulsions, syrups and elixirs may be used, containing inert diluents such as water, ethanol, glycerol, vegetable oils or liquid paraffin. These compositions can comprise substances other than diluents, for example wetting, sweetening, thickening, flavoring or stabilizing products.

The sterile compositions for parenteral administration can preferably be solutions, aqueous or non-aqueous, suspensions or emulsions. As a solvent or vehicle, water, propylene glycol, a polyethylene glycol, vegetable oils, especially olive oil, injectable organic esters, for example ethyl oleate, or other suitable organic solvents may be employed. These compositions can also contain adjuvants, especially wetting, tonicity, emulsifying, dispersing and stabilizing agents. The sterilization may be carried out in several ways, for example by aseptic filtration, by incorporation of sterilizing agents in the composition, by irradiation or by heating. They may also be prepared in the form of sterile solid compositions which can be dissolved at the time of use in sterile water or any other sterile injectable medium.

The doses depend on the effect sought, the treatment period and the administration route used; they are generally between 50 and 800 mg per day via the oral route for an adult, with single doses ranging from 25 to 200 mg of active substance, and between 25 and 600 mg per day via the intravenous route for an adult, with single doses ranging from 12.5 to 200 mg of active substance.

Generally speaking, the doctor will determine the appropriate dosage in accordance with the age, the weight and all other factors specific to the subject to be treated.

The examples which follow illustrate medicinal products according to the invention:

EXAMPLE A

Tablets containing a 50 mg dose of active product and having the following composition are prepared according to the usual technique:

| | |
|---|---|
| Riluzole | 50 mg |
| Mannitol | 64 mg |
| Microcrystalline cellulose | 50 mg |
| Povidone excipient | 12 mg |
| Sodium carboxymethylstarch | 16 mg |
| Talc | 4 mg |
| Magnesium stearate | 2 mg |
| Colloidal silica, anhydrous | 2 mg |
| Mixture of methylhydroxypropyl-cellulose, polyethylene glycol 6000 and titanium dioxide (72:3.5:24.5) q.s. 1 finished film-coated tablet weighing 245 mg | |

EXAMPLE B

Hard gelatin capsules containing a 50 mg dose of active product and having the following composition are prepared according to the usual technique:

| | |
|---|---|
| Riluzole | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE C

An injection containing 10 mg of active product and having the following composition is prepared:

| | | |
|---|---|---|
| Riluzole | | 10 mg |
| Benzoic acid | | 80 mg |
| Benzyl alcohol | | 0.06 cm$^3$ |
| Sodium benzoate | | 80 mg |
| Ethanol, 95% | | 0.4 cm$^3$ |
| Sodium hydroxide | | 24 mg |
| Propylene glycol | | 1.6 cm$^3$ |
| Water | q.s. | 4 cm$^3$ |

The invention also relates to the process for preparing medicinal products which can be used in the treatment of neurological lesions associated with trauma, and especially with spinal, cranial or craniospinal trauma, consisting in mixing riluzole or the pharmaceutically acceptable salts of this compound with one or more compatible and pharmaceutically acceptable diluents and/or adjuvants.

The invention also relates to a method for treating a mammal, and in particular man, having neurological lesions associated with trauma, and especially with spinal, cranial or craniospinal trauma, comprising the administration of an effective amount of riluzole or the pharmaceutically acceptable salts of this compound.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A method for the treatment of neurological lesions associated with trauma, said method comprising treating a patient in need of such treatment with a pharmaceutical composition containing an effective amount of riluzole or the pharmaceutically acceptable salts thereof.

2. A method according to claim 1, wherein the neurological lesions result from spinal cord trauma.

3. A method according to claim 1, wherein the neurological lesions result from cranial trauma.

4. A method according to claim 1, wherein the neurological lesions result from craniospinal trauma.

5. A method according to claim 1, wherein said pharmaceutical composition comprises 25 to 200 mg of riluzole, and may be administered orally.

6. A method according to claim 1, wherein said pharmaceutical composition comprises 12.5 to 200 mg of riluzole and may be administered intravenously.

* * * * *